(12) United States Patent
Zhang et al.

(10) Patent No.: US 12,315,144 B2
(45) Date of Patent: May 27, 2025

(54) ENDOSCOPIC IMAGE PROCESSING METHOD AND APPARATUS, ELECTRONIC DEVICE, AND STORAGE MEDIUM

(71) Applicant: TENCENT TECHNOLOGY (SHENZHEN) COMPANY LIMITED, Shenzhen (CN)

(72) Inventors: Zijian Zhang, Shenzhen (CN); Hong Shang, Shenzhen (CN); Zhongqian Sun, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 549 days.

(21) Appl. No.: 17/676,680

(22) Filed: Feb. 21, 2022

(65) Prior Publication Data

US 2022/0230311 A1 Jul. 21, 2022

Related U.S. Application Data

(63) Continuation of application No. PCT/CN2020/130769, filed on Nov. 23, 2020.

(30) Foreign Application Priority Data

Jan. 23, 2020 (CN) .......................... 202010076394.4

(51) Int. Cl.
  *G06T 7/00* (2017.01)
  *G06T 3/40* (2024.01)
(52) U.S. Cl.
  CPC .............. *G06T 7/0012* (2013.01); *G06T 3/40* (2013.01); *G06T 2207/10016* (2013.01); *G06T 2207/10068* (2013.01); *G06T 2207/30096* (2013.01)

(58) Field of Classification Search
  CPC ................... G06T 7/0012; G06T 3/40; G06T 2207/10016; G06T 2207/10068; G06T 2207/30096
  See application file for complete search history.

(56) References Cited

U.S. PATENT DOCUMENTS

9,402,601 B1 * 8/2016 Berger .................. G16H 40/67
10,671,934 B1 * 6/2020 Ninh ........................ G06N 5/04
(Continued)

FOREIGN PATENT DOCUMENTS

| CN | 108509248 A | 9/2018 |
| CN | 108805834 A | 11/2018 |

(Continued)

OTHER PUBLICATIONS

China National Intellectual Property Administration (CNIPA) Office Action 1 for 202010076394.4 Jan. 11, 2023 12 Pages (including translation).

(Continued)

*Primary Examiner* — Kevin Ky
(74) *Attorney, Agent, or Firm* — ANOVA LAW GROUP, PLLC

(57) ABSTRACT

This application provides an endoscopic image processing method and apparatus, an electronic device, and a storage medium. The method includes: obtaining an endoscopic video stream, the endoscopic video stream including an original endoscopic image; detecting the original endoscopic image in a corresponding video frame through a first thread, and transmitting a detection result of the original endoscopic image to an integration module; forming a control instruction through the integration module according to the detection result; and adjusting, in response to the control instruction and through a second thread, an output result in the second thread, the output result corresponding (Continued)

to a use environment of the endoscopic video stream, the first thread and the second thread being parallel threads.

18 Claims, 8 Drawing Sheets

(56) References Cited

U.S. PATENT DOCUMENTS

| | | | |
|---|---|---|---|
| 10,904,429 B2 | 1/2021 | Kobayashi et al. | |
| 2002/0022658 A1* | 2/2002 | Das | A61K 31/557 |
| | | | 514/549 |
| 2004/0015079 A1* | 1/2004 | Berger | G01S 7/5208 |
| | | | 600/443 |
| 2008/0128492 A1* | 6/2008 | Roth | G06Q 30/018 |
| | | | 235/380 |
| 2009/0088634 A1 | 4/2009 | Zhao et al. | |
| 2012/0217410 A1* | 8/2012 | Amitani | H04N 5/32 |
| | | | 250/370.09 |
| 2013/0273968 A1* | 10/2013 | Rhoads | H04W 4/50 |
| | | | 455/566 |
| 2015/0080652 A1 | 3/2015 | Staples et al. | |
| 2015/0146920 A1 | 5/2015 | Mazurenko et al. | |
| 2016/0163064 A1 | 6/2016 | Ruf et al. | |
| 2018/0144453 A1 | 5/2018 | Koiso | |
| 2018/0250094 A1 | 9/2018 | Sugie et al. | |
| 2018/0253839 A1 | 9/2018 | Zur | |
| 2019/0095679 A1* | 3/2019 | Aragaki | G06T 7/187 |
| 2019/0114804 A1 | 4/2019 | Sundaresan et al. | |
| 2020/0012171 A1* | 1/2020 | Yoshino | G03B 7/003 |
| 2020/0058124 A1* | 2/2020 | Iwaki | G06T 7/0012 |
| 2020/0135330 A1* | 4/2020 | Sugie | G06V 10/147 |
| 2020/0169672 A1* | 5/2020 | Li | H04N 23/951 |
| 2020/0184644 A1* | 6/2020 | Ueda | G16H 50/20 |
| 2020/0320702 A1* | 10/2020 | Kamon | A61B 1/0638 |
| 2021/0022586 A1 | 1/2021 | Mori et al. | |
| 2021/0192738 A1* | 6/2021 | Meguro | G06T 7/0012 |
| 2022/0230311 A1* | 7/2022 | Zhang | G06T 3/40 |
| 2024/0193873 A1* | 6/2024 | Chenna Madhavuni | |
| | | | G06T 7/73 |
| 2024/0389977 A1* | 11/2024 | Hamano | A61B 8/14 |

FOREIGN PATENT DOCUMENTS

| | | |
|---|---|---|
| CN | 108852286 A | 11/2018 |
| CN | 109919988 A | 6/2019 |
| CN | 109993769 A | 7/2019 |
| CN | 110211152 A | 9/2019 |
| CN | 110634564 A | 12/2019 |
| CN | 111311557 A | 6/2020 |
| JP | 201879249 A | 5/2018 |
| JP | 201892495 A | 6/2018 |
| WO | 2017042812 A2 | 3/2017 |
| WO | 2019198808 A1 | 10/2019 |

OTHER PUBLICATIONS

The Japan Patent Office (JPO) Notification of Reasons for Refusal for Application No. 2022-523504 and Translation Feb. 1, 2023 8 Pages.
The European Patent Office (EPO) The Extended European Search Report for 20914926.9 May 31, 2023 16 Pages (including translation).
Zhang Zijian et al : "Asynchronous in Parallel Detection and Tracking (AIPDT):Real-Time Robust Polyp Detection",arxiv.org,vol. 69, No. 505214,Sep. 29, 2020 (Sep. 29, 2020), pp. 722-731, XP047594648.
Fan Heng et al : "Parallel Tracking and Verifying: A Framework for Real-Time and High Accuracy Visual Tracking", 2017 IEEE International Conference on Computer Vision (ICCV), IEEE,Oct. 22, 2017 (Oct. 22, 2017), pp. 5487-5495, XP033283428,DOI: 10.1109/ICCV.2017.585 [retrieved on Dec. 22, 2017].
Liu Shasha et al : "Embedded Online Fish Detection and Tracking System via YOLOv3 and Parallel Correlation Filter", OCEANS 2018 MTS/IEEE Charleston, IEEE,Oct. 22, 2018 (Oct. 22, 2018), pp. 1-6,XP033494568, DOI: 10.1109/OCEANS.2018.8604658 [retrieved on Jan. 7, 2019].
Zheng He et al : "Polyp Tracking in Video Colonoscopy Using Optical Flow With an On-The-Fly Trained CNN", 2019 IEEE 16th International Symposium on Biomedical Imaging (ISBI 2019), IEEE,Apr. 8, 2019 (Apr. 8, 2019), pp. 79-82,XP033576312,DOI: 10.1109/ISBI.2019.8759180.
Yamada Masayoshi et al.: "Development of a real-time endoscopic image diagnosis support system using deep learning technology in colonoscopy", Scientific Reports, [Online] vol. 9, No. 1, Dec. 2019 (Dec. 2019), p. 14465, XP055943421,DOI: 10.1038/s41598-019-50567-5 Retrieved from the Internet : URL :https ://www.nature.com/articles/s41598-019-50567-5.pdf> [retrieved on Jul. 18, 2022].
The World Intellectual Property Organization (WIPO) International Search Report for PCT/CN2020/130769 Feb. 23, 2021 6 Pages (including translation).

* cited by examiner

ENDOSCOPIC IMAGE PROCESSING METHOD AND APPARATUS, ELECTRONIC DEVICE, AND STORAGE MEDIUM

RELATED APPLICATIONS

This application claims priority to PCT Application No. PCT/CN2020130769, filed on Nov. 23, 2020, which claims priority to Chinese Patent Application No. 202010076394.4 filed on Jan. 23, 2020. The two applications are incorporated herein by reference by their entirety.

FIELD OF THE TECHNOLOGY

This application relates to medical image processing technologies, and in particular, to an artificial intelligence technology-based endoscopic image processing method and apparatus, an electronic device, and a storage medium.

BACKGROUND OF THE DISCLOSURE

Category identification performed based on deep learning is always an important tool for resolving classification of a large amount of data in various application scenarios. For example, in application scenarios such as image processing and natural language processing, large-scale classification and identification of a large amount of data may be implemented, to obtain a related classification prediction result and accelerate the implementation of functions in the application scenarios rapidly and accurately.

Various medical images are generated and processed. For example, images are generated continuously as an endoscope continuously performs photographing in a digestive tract, and the images further become a large amount of data. Therefore, large-scale classification and identification with the aid of execution of classification prediction are needed to process the image data.

In the related art, a target detection model (using various types of target detection algorithms such as Retina Net, FasterRCNN, and YOLO) with relatively high accuracy is generally integrated in a solution to implementing target detection on a real-time video stream (such as a colon endoscopic video stream), and image frames in the video stream are sequentially inputted into the model for target detection. However, the processing speed of the model is limited, and the processing speed of the model cannot match a speed of the real-time video stream. Therefore, in the related art, the detection model cannot match a frame rate of a real-time video, thereby impairing the performance of the model.

SUMMARY

In view of this, embodiments consistent with this disclosure provide an endoscopic image processing method and apparatus, an electronic device, and a storage medium, which can process an original endoscopic image through a first thread and a second thread that are parallel, to cause an output result to match a use environment of an endoscopic video stream.

The technical solutions in the embodiments consistent with this disclosure are implemented as follows:

One aspect of this application provides an endoscopic image processing method. The method includes: obtaining an endoscopic video stream, the endoscopic video stream including an original endoscopic image; detecting the original endoscopic image in a corresponding video frame through a first thread, and transmitting a detection result of the original endoscopic image to an integration module; forming a control instruction through the integration module according to the detection result; and adjusting, in response to the control instruction and through a second thread, an output result in the second thread, the output result corresponding to a use environment of the endoscopic video stream, the first thread and the second thread being parallel threads.

Another aspect of this application further provides an endoscopic image processing method, including: obtaining, by an endoscopic image processing apparatus, an endoscopic video stream transmitted by an endoscope, the endoscopic video stream including an original endoscopic image used for observing a corresponding lesion of a target object; detecting, by the endoscopic image processing apparatus, the original endoscopic image in a corresponding video frame through a first thread, and transmitting a detection result of the original endoscopic image to an integration module; forming, by the endoscopic image processing apparatus, a control instruction through the integration module according to the detection result; adjusting, by the endoscopic image processing apparatus in response to the control instruction and through a second thread, an output result in the second thread, the output result corresponding to a use environment of the endoscopic video stream, the first thread and the second thread being parallel threads; and transmitting, by the endoscopic image processing apparatus according to an adjusted output result in the second thread, a corresponding target endoscopic image frame to a medical device in contact with the target object, and outputting, by the medical device, the corresponding target endoscopic image frame.

An embodiment of this application further provides an electronic device, including: a memory, configured to store executable instructions; and a processor, configured to, when executing the executable instructions stored in the memory, perform: obtaining, by an endoscopic image processing apparatus, an endoscopic video stream transmitted by an endoscope, the endoscopic video stream including an original endoscopic image used for observing a corresponding lesion of a target object; detecting, by the endoscopic image processing apparatus, the original endoscopic image in a corresponding video frame through a first thread, and transmitting a detection result of the original endoscopic image to an integration module; forming, by the endoscopic image processing apparatus, a control instruction through the integration module according to the detection result; adjusting, by the endoscopic image processing apparatus in response to the control instruction and through a second thread, an output result in the second thread, the output result corresponding to a use environment of the endoscopic video stream, the first thread and the second thread being parallel threads; and transmitting, by the endoscopic image processing apparatus according to an adjusted output result in the second thread, a corresponding target endoscopic image frame to a medical device in contact with the target object, and outputting, by the medical device, the corresponding target endoscopic image frame.

An embodiment consistent with this disclosure further provides a non-transitory computer-readable storage medium, storing executable instructions, the executable instructions, when executed by a processor, implementing the foregoing endoscopic image processing method.

The embodiments consistent with this disclosure have the following beneficial effects.

An endoscopic video stream is obtained, where the endoscopic video stream includes an original endoscopic image; the original endoscopic image in a corresponding video frame is detected through a first thread, and a detection result of the original endoscopic image is transmitted to an integration module; a control instruction is formed through the integration module according to the detection result of the original endoscopic image; and in response to the control instruction and through a second thread, an output result in the second thread is adjusted. This application can control the output result to match a use environment of the endoscopic video stream through a first thread and a second thread that are parallel, thereby improving real-time accuracy of processing of the endoscopic images and improving the real-time recall rate.

BRIEF DESCRIPTION OF THE DRAWINGS

To describe the technical solutions of the embodiments consistent with this disclosure or the related art more clearly, the following briefly introduces the accompanying drawings required for describing the embodiments or the related art. The accompanying drawings in the following description show merely some embodiments consistent with this disclosure, and a person of ordinary skill in the art may still derive other accompanying drawings from these accompanying drawings without creative efforts.

DESCRIPTION OF EMBODIMENTS

To make the objectives, technical solutions, and advantages of this application clearer, the following further describes this application in detail with reference to the accompanying drawings. The described embodiments are not to be considered as a limitation to this application. All other embodiments obtained by a person of ordinary skill in the art without creative efforts shall fall within the protection scope of this application.

In the following descriptions, the term "some embodiments" describes subsets of all possible embodiments, but it may be understood that "some embodiments" may be the same subset or different subsets of all the possible embodiments, and can be combined with each other without conflict.

Before the embodiments consistent with this disclosure are further described in detail, a description is made on nouns and terms in the embodiments consistent with this disclosure, and the nouns and terms in the embodiments consistent with this disclosure are applicable to the following explanations.

1) "In response to" is used for representing a condition or status on which one or more operations to be performed depend. When the condition or status is satisfied, the one or more operations may be performed in real time or after a set delay. Unless explicitly stated, there is no limitation on the order in which the plurality of operations are performed.

2) "Computer-aided diagnosis (CAD)" is used for finding a lesion with the aid of imaging, medical image processing technologies, and other possible physical or biochemical methods in combination with analytical calculation of a computer, to improve the accuracy of diagnosis.

3) "Endoscopic video stream" is used for pathological information in a video state formed by performing image acquisition on body parts (different target organs of a human body or lesions in a human body) through an image acquisition device (such as an endoscope).

4) "Lesion" generally refers to a body part with a pathological change. In other words, a limited pathological tissue with pathogenic microbes may be referred to as a lesion.

5) "YUV" is a grayscale value encoding method, which is a color encoding method, where "Y" represents luminance or luma, namely, a grayscale value, "U" and "V" represent chrominance or chroma, and functions thereof are to describe colors and saturation of an image and are used to specify colors of pixels.

6) "RGB" refers to a three-primary color encoding method and is also referred to as an RGB color mode, which is a color standard in the industry, and obtains various colors through changes of a red (R) channel, a green (G) channel, and a blue (B) channel and superpositions of the three color channels. RGB represents colors of the red channel, the green channel, and the blue channel, and this standard almost covers all colors that human eyes can perceive and is one of the most widely used color systems.

Figure 1:
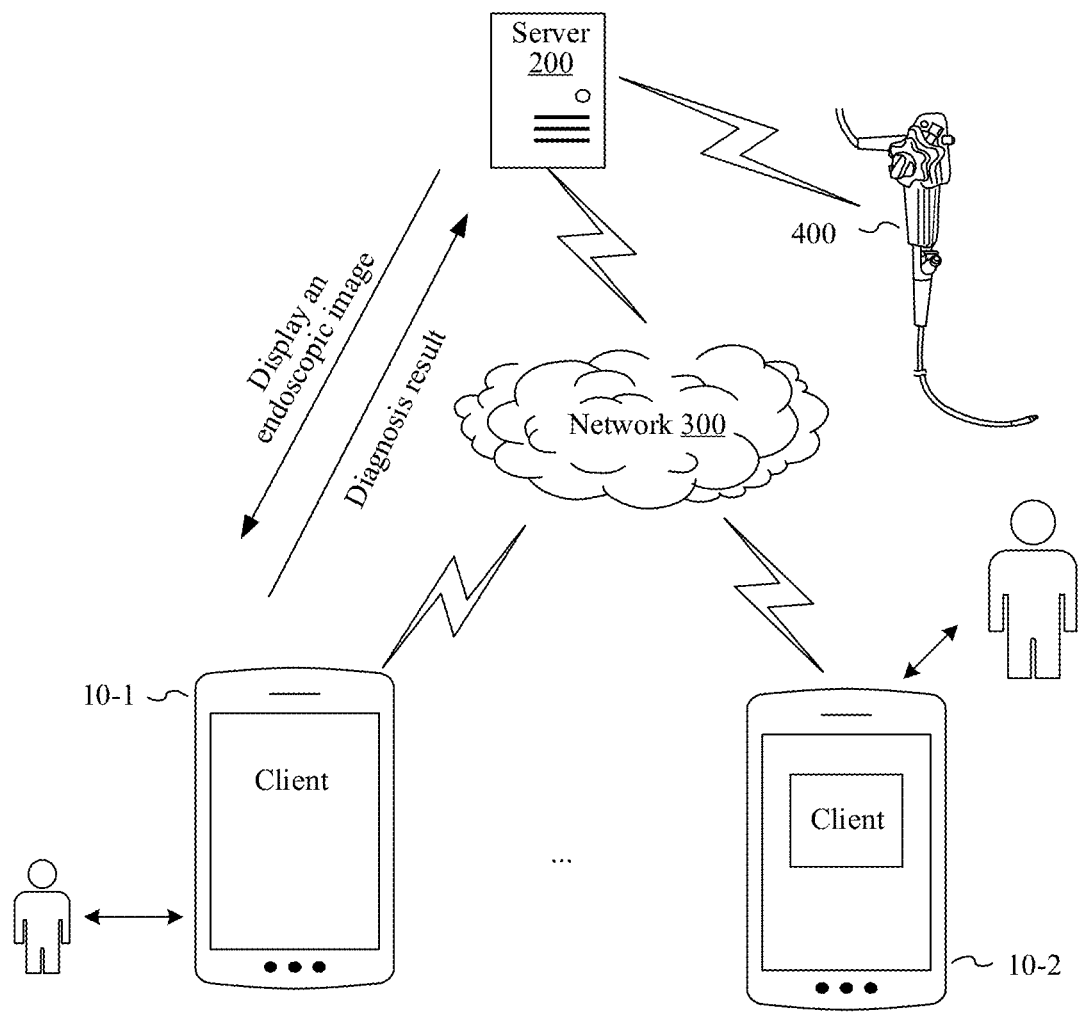
FIG. 1 is a schematic diagram of a use environment of an endoscopic image processing method according to an embodiment consistent with this disclosure.

FIG. 1 is a schematic diagram of a use scenario of an endoscopic image processing method according to an embodiment consistent with this disclosure. Referring to FIG. 1, corresponding client applications that can execute different functions are disposed on a terminal (including a terminal 10-1 and a terminal 10-2), the client applications are used for the terminal (including the terminal 10-1 and the terminal 10-2) to obtain different pathological information from a corresponding server 200 through a network 300 for browsing. The terminal is connected to the server 200 through the network 300, the network 300 may be a wide area network or a local area network or may be a combination thereof to implement data transmission by using a wireless link. Types of the pathological information obtained by the terminal (including the terminal 10-1 and the terminal 10-2) from the corresponding server 200 through the network 300 may be the same or may be different. For example, the terminal (including the terminal 10-1 and the terminal 10-2) may both obtain a pathological image or a pathological video matching a target object from the corresponding server 200 through the network 300, or may only obtain a pathological video (for example, an endoscopic video stream) matching a current target from the corresponding server 200 through the network 300 for browsing. The server 200 may store pathological information corresponding to different target objects, or may store auxiliary analytical information matching the pathological information of the target objects. In some embodiments consistent with this disclosure, different types of pathological information stored in the server 200 may be endoscopic video streams acquired by an endoscope. There are at least two original endoscopic images in the endoscopic video stream of this embodiment. The endoscopic video stream is a collection of multi-field-of-view pathological pictures obtained by repeatedly observing suspected lesion regions when a doctor uses an endoscope by moving a camera, switching magnifications and other operations, and the collection combines information under a specific field of view of the endoscope. Because the endoscopic video stream records all the information in the field of view of the endoscope when the doctor observes a lesion of a patient, the information of a lesion of a single patient observed by the doctor in the field of view of the endoscope is used as a continuous video stream to prevent the doctor from ignoring tiny lesion regions when rapidly moving the endoscope. Therefore, the endoscopic video stream provides more information than a single-frame picture does, to help the doctor diagnose and find tiny lesion regions.

The patient lesions observation under the endoscope (a medical device in contact with the target object) may include a plurality of different use scenarios, for example, screening of video streams for diabetic retinopathy screening and cervical cancer early screening. The endoscopic image processing method based on this embodiment may be deployed to a plurality of application scenarios, thereby making it convenient for a doctor to consult and use remotely.

The server 200 transmits pathological information of the same target object to the terminal (the terminal 10-1 and/or the terminal 10-2) through the network 300, to enable a user of the terminal (the terminal 10-1 and/or the terminal 10-2) to analyze the pathological information of the target object. Therefore, as an example, the server 200 is provided with a corresponding neural network model, configured to obtain a video stream of an endoscope device 400, the endoscopic video stream carrying an original endoscopic image. The server 200 may detect the original endoscopic image in a corresponding video frame through a first thread, and transmit a detection result of the original endoscopic image to an integration module; form a control instruction through the integration module according to the detection result of the original endoscopic image; and adjust, in response to the control instruction and through a second thread, an output result in the second thread, to cause the output result to match a use environment of the endoscopic video stream, the first thread and the second thread being parallel threads.

Figure 2:
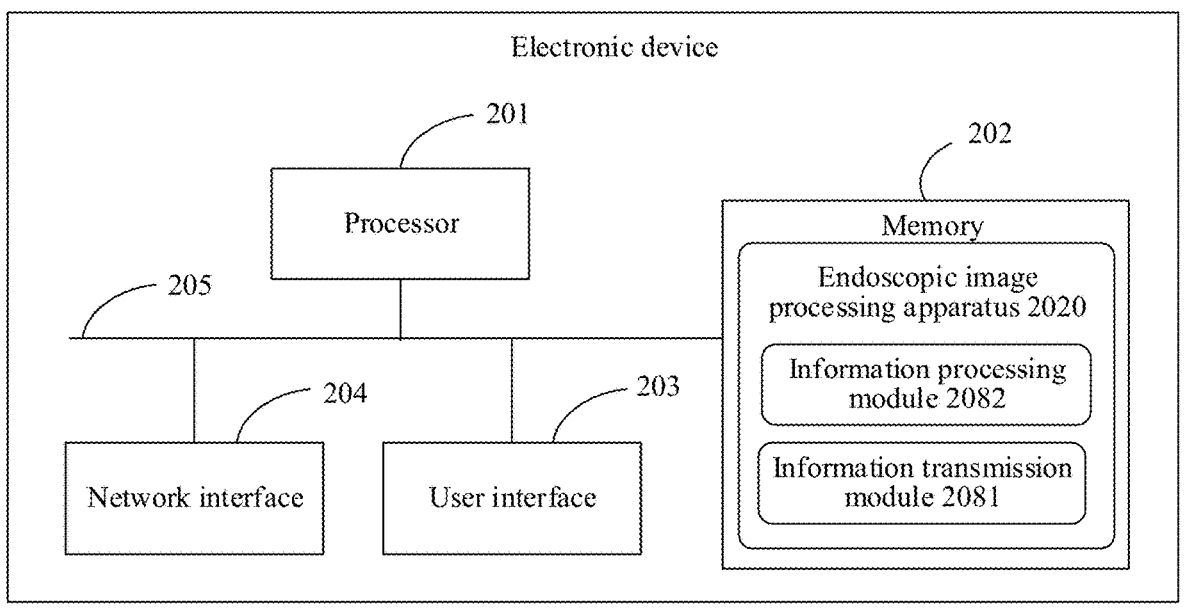
FIG. 2 is a schematic structural diagram of components of an electronic device according to an embodiment consistent with this disclosure.

The following describes a structure of the electronic device according to the embodiments consistent with this disclosure in detail. The electronic device may be implemented in various forms. For example, the electronic device may be a dedicated terminal with an endoscopic image processing function, or an electronic device or cloud server with an endoscopic image processing function, such as the server 200 in FIG. 1. FIG. 2 is a schematic structural diagram of components of an electronic device according to an embodiment consistent with this disclosure. It may be understood that, FIG. 2 shows only an exemplary structure rather than a complete structure of the electronic device. The structure shown in FIG. 2 may be partially or entirely implemented based on requirements.

The electronic device provided in this embodiment consistent with this disclosure includes: at least one processor 201, a memory 202, a user interface 203, and at least one network interface 204. The components in the electronic device are coupled by using a bus system 205. It may be understood that, the bus system 205 is configured to implement connection and communication between the components. In addition to a data bus, the bus system 205 further includes a power bus, a control bus, and a state signal bus. However, for ease of clear description, all types of buses are labeled as the bus system 205 in FIG. 2.

The user interface 203 may include a display, a keyboard, a mouse, a track ball, a click wheel, a key, a button, a touch panel, a touchscreen, or the like.

It may be understood that, the memory 202 may be a volatile memory or a non-volatile memory, or may include both a volatile memory and a non-volatile memory. The memory 202 in this embodiment consistent with this disclosure can store data to support operations of the terminal (for example, 10-1). An example of the data includes any computer program to be operated on the terminal (for example, 10-1), for example, an operating system and an application program. The operating system includes various system programs, such as a framework layer, a kernel library layer, and a driver layer, which are configured to implement various basic services and process a task based on hardware. The application program may include various application programs.

In some embodiments, the endoscopic image processing apparatus provided in the embodiments consistent with this disclosure may be implemented by a combination of software and hardware. For example, the endoscopic image processing apparatus provided in the embodiments consistent with this disclosure may be a processor in the form of a hardware decoding processor, and is programmed to perform the endoscopic image processing method provided in the embodiments consistent with this disclosure. For example, the processor in the form of a hardware decoding processor may use one or more application specific integrated circuits (ASICs), digital signal processors (DSPs), programmable logic devices (PLDs), complex programmable logic devices (CPLDs), field-programmable gate arrays (FPGAs), or other electronic elements.

In an example in which the endoscopic image processing apparatus provided in the embodiments consistent with this disclosure is implemented by a combination of software and hardware, the endoscopic image processing apparatus provided in the embodiments consistent with this disclosure may be directly embodied as a combination of software modules executed by the processor 201. The software module may be located in a storage medium, the storage medium is located in the memory 202, and the processor 201 reads executable instructions included in the software module in the memory 202, and implements, in combination with necessary hardware (for example, including the processor 201 and another component connected to the bus 205), the endoscopic image processing method provided in the embodiments consistent with this disclosure.

For example, the processor 201 may be an integrated circuit chip, and has a signal processing capability, for example, a general-purpose processor, a DSP, or another PLD, a discrete gate or a transistor logical device, or a discrete hardware component. The general-purpose processor may be a microprocessor, any conventional processor, or the like.

In an example in which the endoscopic image processing apparatus provided in the embodiments consistent with this disclosure is implemented by hardware, the apparatus provided in the embodiments consistent with this disclosure may be directly executed by using the processor 201 in the form of a hardware decoding processor, for example, one or more ASICs, DSPs, PLDs, CPLDs, FPGAs, or other electronic elements, to execute the endoscopic image processing method provided in the embodiments consistent with this disclosure.

The memory 202 in this embodiment consistent with this disclosure is configured to store various types of data to support operations of the electronic device. An example of the data includes: any executable instruction configured to be operated on the electronic device, such as an executable instruction, and a program that implements the endoscopic image processing method of the embodiments consistent with this disclosure may be included in the executable instruction.

In some other embodiments, the endoscopic image processing apparatus provided in the embodiments consistent with this disclosure may be implemented in the form of software. FIG. 2 shows an endoscopic image processing apparatus 2020 stored in the memory 202, which may be software in the form of a program, a plug-in, or the like, and include a series of modules. An example of the program stored in the memory 202 may include the endoscopic image processing apparatus 2020. The endoscopic image processing apparatus 2020 includes the following software modules:

an information transmission module 2081, configured to obtain an endoscopic video stream, the endoscopic video stream carrying an original endoscopic image;

an information processing module 2082, configured to detect the original endoscopic image in a corresponding video frame through a first thread, and transmit a detection result of the original endoscopic image to an integration module;

the information processing module 2082 being configured to form a control instruction through the integration module according to the detection result of the original endoscopic image; and the information processing module 2082 being configured to adjust, in response to the control instruction and through a second thread, an output result in the second thread, to cause the output result to match a use environment of the endoscopic video stream, the first thread and the second thread being parallel threads.

Figure 3:
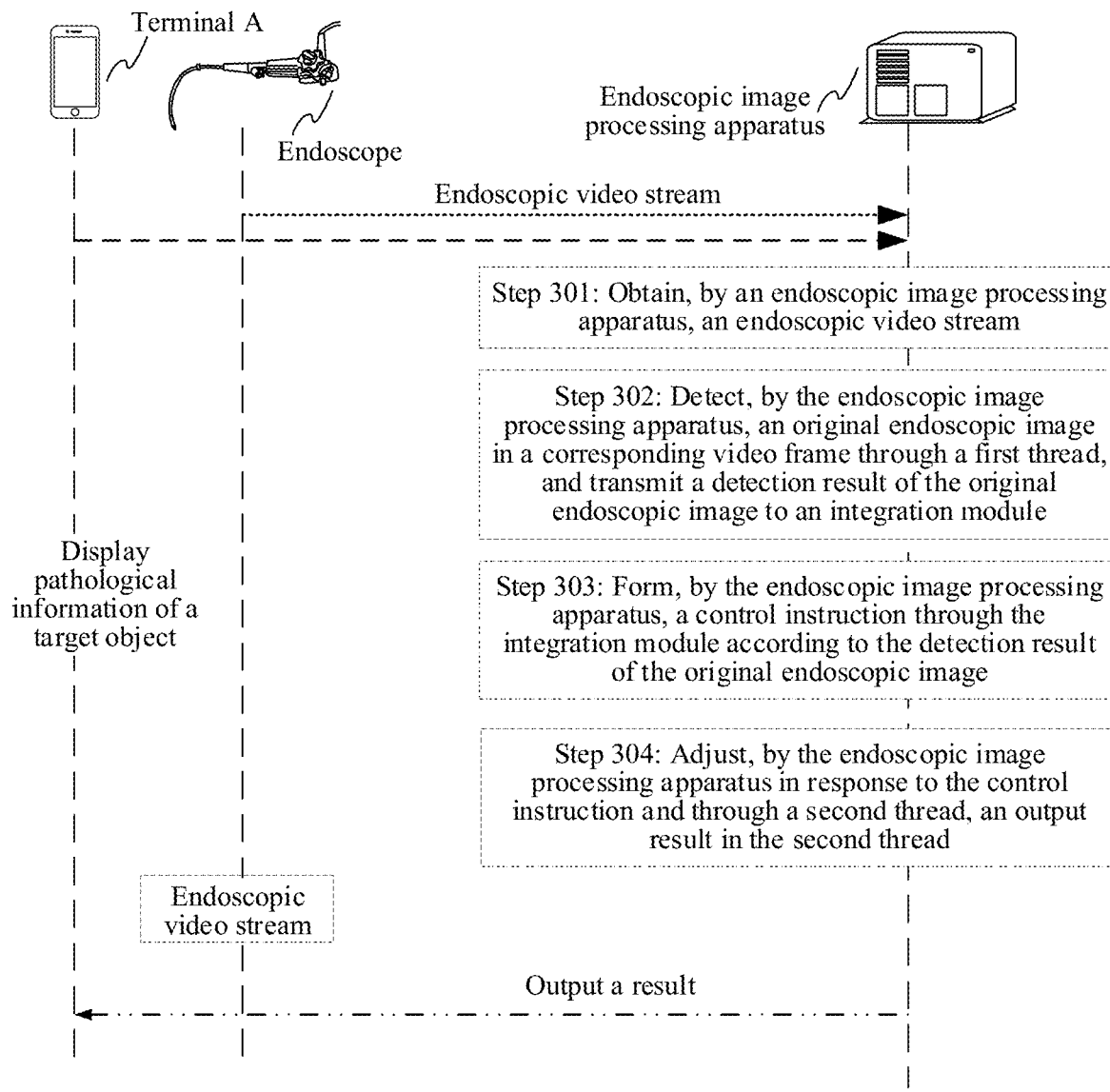
FIG. 3 is a schematic flowchart of an endoscopic image processing method according to an embodiment consistent with this disclosure.

The endoscopic image processing method provided in the embodiments consistent with this disclosure is described with reference to the electronic device shown in FIG. 2. FIG. 3 is a schematic flowchart of an endoscopic image processing method according to an embodiment consistent with this disclosure. It may be understood that, steps shown in FIG. 3 may be performed by various servers running the endoscopic image processing apparatus, such as a dedicated terminal, a server, a cloud server, or a server cluster with an endoscopic image processing function. The following describes the steps shown in FIG. 3.

Step 301: Obtain, by an endoscopic image processing apparatus, an endoscopic video stream.

The endoscopic video stream carries an original endoscopic image, and the endoscopic video stream is a video stream photographed by an endoscope in a medical setting such as a real use environment in a hospital. Under the movement and photographing of the endoscope, the endoscopic video stream presents video endoscopy captured by a lens of the endoscope. Therefore, a plurality of frames of consecutive original endoscopic images are obtained from the endoscopic video stream, and each frame of obtained original endoscopic image describes video endoscopy photographed by the endoscope at a time point, so that identification on the endoscopic image may be implemented based on each frame of original endoscopic image.

In implemented endoscopic image identification, the endoscope photographs an endoscopic video stream in organism, such as an internal part of a human body. For example, the endoscope photographs an endoscopic video stream in a cavity communicating with the outside or an enclosed cavity. For example, the mentioned cavity communicating with the outside may be a digestive tract, a respiratory tract, or a urinary tract, and the enclosed cavity may be a cavity into which the endoscope needs to be put through an incision such as a chest cavity, an abdominal cavity, or an articular cavity. Organ conditions in a corresponding cavity is obtained through the endoscopic video stream photographing and identification performed by the endoscope. In a process of using the endoscope to check a cavity, an obtained endoscopic video stream is accessed into performed endoscopic image identification. In addition, the implemented endoscopic image identification may be further performed on an endoscopic video stream obtained before such as a historical endoscopic video stream, and the implemented endoscopic image identification is not limited to real-time identification, but may be performed oriented to a large amount of endoscopic video streams that are stored.

In some embodiments consistent with this disclosure, obtaining an endoscopic video stream may be implemented as follows:

extracting an endoscopic video frame in pathological information of a target object; improving resolution of the endoscopic video frame; converting a format of the endoscopic video frame from a current encoding format to a grayscale value encoding format, to obtain a plurality of endoscopic video frames; and performing encoding compression on the endoscopic video frame to form an endoscopic video stream. A plurality of endoscopic video frames are obtained by converting the format of the endoscopic video frame from a current encoding format to a grayscale value encoding format; and encoding compression is performed on all obtained endoscopic video frames to form pathological information in a video state, thereby reducing a data transmission amount and reducing freezing. On the other hand, dynamic fuzzy and picture quality may be improved, and user experience is further improved, and it is helpful for a user (doctor) of a remote terminal to make accurate judgment on the pathological information of the target object more accurately.

In some embodiments consistent with this disclosure, the converting a format of the endoscopic video frame from a current encoding format to a grayscale value encoding format may be implemented as follows:

performing encoding compression on the endoscopic video frame respectively by using an encoding method matching a target format; writing a serial number corresponding to the video frame and generating a timestamp corresponding to an image packet, to generate a packet matching the format of the endoscopic video frame; and splicing the image packet to form a plurality of endoscopic video frames. When encoding compression is performed on each image frame to form a video stream, preset video encoding software such as ffmpeg codec software may be used. The ffmpeg codec software is free software, may run video recording, conversion, and stream functions of a plurality of formats of audio and video, and includes a decoding/encoding library of audio and video. Specifically, encoding compression may be performed on the image frames by using a video compression algorithm in the video encoding software such as H264 or X264 to form a video stream, where H264 or X264 is a digital video compression format and is also a video codec standard. In this process, a YUV format refers to a pixel format that represents luminance parameters and chrominance parameters, and separating the luminance parameters and the chrominance parameters can both avoid mutual interference and reduce a sampling rate of chrominance from greatly affecting image quality. The YUV does not require three independent video signals to be transmitted at the same time as that of the RGB, so that converting image frames into the YUV format for transmission may occupy less bandwidth, thereby saving a large amount of resources. The YUV format is divided into a planar type and a packed type, for the planar YUV format, luminance of all pixels is first stored consecutively, chrominance of all the pixels is then stored, and saturation of all the pixels is finally stored; and for the packed YUV format, luminance, chrominance, and saturation of each pixel are stored consecutively and alternately. For image frames in the YUV format, the image frames may be stored by using a storage format such as YUV422P, YUV420, or YUV420sp, to save storage resources of the terminal device and improve transmission efficiency of pathological information simultaneously.

Further, in a process of transmitting the endoscopic video stream to the terminal device according to a preset transmission protocol, the transmission protocol may be a real-time data transmission protocol such as a user datagram protocol (UDP), where the UDP is a connectionless protocol used for processing packets. In this application, a type of the data transmission protocol is not specifically limited. As some embodiments consistent with this disclosure, the video stream may be transmitted to the terminal device by using the UDP.

In some embodiments consistent with this disclosure, the method further includes:

adjusting the original endoscopic image to a target size to generate standard endoscopic image frames; and filtering the standard endoscopic image frames and deleting a standard endoscopic image frame having interference, to form a target endoscopic image frame comprising different target endoscopic image frames.

Step 302: Detect, by the endoscopic image processing apparatus, an original endoscopic image in a corresponding video frame through a first thread, and transmit a detection result of the original endoscopic image to an integration module.

Step 303: Form, by the endoscopic image processing apparatus, a control instruction through the integration module according to the detection result of the original endoscopic image.

Step 304: Adjust, by the endoscopic image processing apparatus in response to the control instruction and through a second thread, an output result in the second thread.

The first thread and the second thread are parallel threads.

The output result may match a use environment of the endoscopic video stream.

Figure 4A:
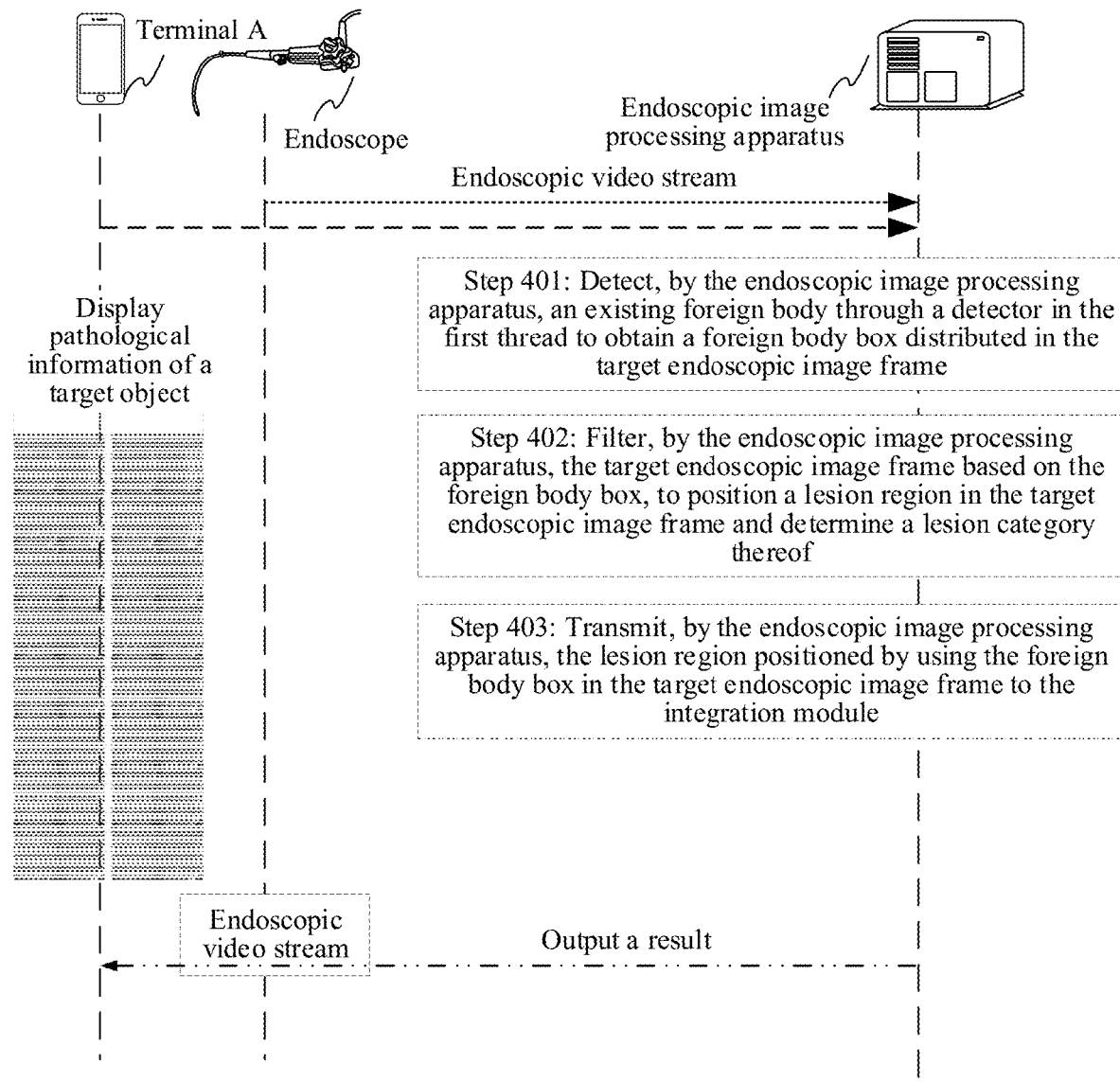
FIG. 4A is a schematic flowchart of an endoscopic image processing method according to an embodiment consistent with this disclosure.

The endoscopic image processing method provided in the embodiments consistent with this disclosure is described with reference to the electronic device shown in FIG. 2. FIG. 4A is a schematic flowchart of an endoscopic image processing method according to an embodiment consistent with this disclosure. It may be understood that, steps shown in FIG. 4A may be performed by various servers running the endoscopic image processing apparatus, such as a dedicated terminal, a server, a cloud server, or a server cluster with an endoscopic image processing function. The following describes steps shown in FIG. 4A.

Step 401: Detect, by the endoscopic image processing apparatus, a foreign body through a detector in the first thread to obtain a foreign body box distributed in the target endoscopic image frame.

The foreign body box is used for indicating a region where a foreign body exists in the target endoscopic image frame.

Step 402: Filter, by the endoscopic image processing apparatus, the target endoscopic image frame based on the foreign body box, to position a lesion region in the target endoscopic image frame and determine a lesion category thereof.

Step 403: Transmit, by the endoscopic image processing apparatus, the lesion region positioned by using the foreign body box in the target endoscopic image frame to the integration module.

In some embodiments consistent with this disclosure, the endoscopic image processing method further includes:

when a detection time of the detector in the first thread exceeds a detection time threshold, stopping detecting a current target endoscopic image frame, and obtaining a subsequent target endoscopic image frame for detection.

In some embodiments consistent with this disclosure, the adjusting, in response to the control instruction and through a second thread, an output result in the second thread may be implemented as follows:

when a tracker in the second thread is in a continuation state and a tracking box corresponding to the tracker matches a foreign body box corresponding to a detector, outputting, by the tracker in the second thread, a current target endoscopic image frame.

In some embodiments consistent with this disclosure, the adjusting, in response to the control instruction and through a second thread, an output result in the second thread may be implemented as follows:

when a tracker in the second thread is in a re-initiation state and a tracking box corresponding to the tracker does not match a foreign body box corresponding to a detector, outputting, by the tracker in the second thread, a new target endoscopic image frame.

In some embodiments consistent with this disclosure, the endoscopic image processing method further includes:

determining a corresponding box regression parameter when it is determined through the detector in the first thread that a foreign body box exists in the target endoscopic image frame; and activating the tracker in the second thread by using the box regression parameter.

In some embodiments consistent with this disclosure, the endoscopic image processing method further includes:

when the tracker in the second thread is activated, distributing a target identifier to a foreign body in the current target endoscopic image frame; and when foreign bodies in target endoscopic image frames when the tracker in the second thread is in an activated state, a continuation state, and a re-initiation state are consistent, initializing the target identifier to implement continuous tracking on the foreign body in the current target endoscopic image frame.

In some embodiments consistent with this disclosure, the endoscopic image processing method further includes:

transmitting an adjustment instruction in response to the output result in the second thread, the adjustment instruction being used for adjusting a detection state of a medical device in contact with a target object, to obtain new pathological information.

Figure 4B:
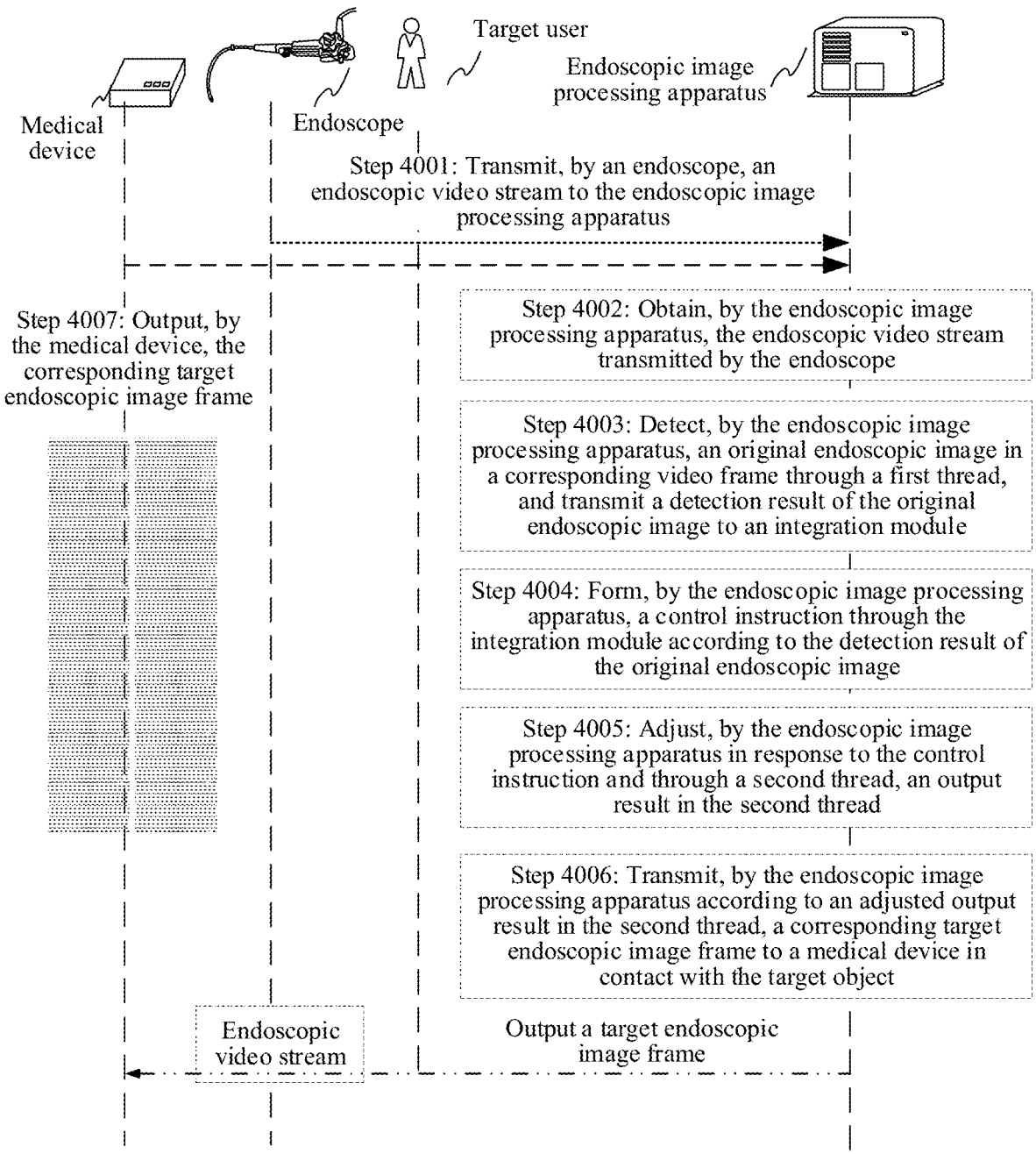
FIG. 4B is a schematic flowchart of an endoscopic image processing method according to an embodiment consistent with this disclosure.

The endoscopic image processing method provided in the embodiments consistent with this disclosure is described in an endoscopic image processing system with reference to the electronic device shown in FIG. 2. FIG. 4B is a schematic flowchart of an endoscopic image processing method according to an embodiment consistent with this disclosure. It may be understood that, steps shown in FIG. 4B may be performed by various servers running the endoscopic image processing apparatus, such as a dedicated terminal, a server, a cloud server, or a server cluster with an endoscopic image processing function. The following describes the steps shown in FIG. 4B.

Step 4001: Transmit, by an endoscope, an endoscopic video stream to the endoscopic image processing apparatus.

Step 4002: Obtain, by the endoscopic image processing apparatus, the endoscopic video stream transmitted by the endoscope.

The endoscopic video stream carrying an original endoscopic image used for observing a corresponding lesion of a target object.

Step 4003: Detect, by the endoscopic image processing apparatus, an original endoscopic image in a corresponding video frame through a first thread, and transmit a detection result of the original endoscopic image to an integration module.

Step 4004: Form, by the endoscopic image processing apparatus, a control instruction through the integration module according to the detection result of the original endoscopic image.

Step 4005: Adjust, by the endoscopic image processing apparatus in response to the control instruction and through a second thread, an output result in the second thread.

The output result may match a use environment of the endoscopic video stream, and the first thread and the second thread are parallel threads.

Step 4006: Transmit, by the endoscopic image processing apparatus according to an adjusted output result in the second thread, a corresponding target endoscopic image frame to a medical device in contact with the target object.

Step 4007: Output, by the medical device, the corresponding target endoscopic image frame.

According to the technical solution shown in this embodiment, the output result is controlled to match a use environment of the endoscopic video stream through a first thread and a second thread that are parallel, thereby improving real-time accuracy of processing on the endoscopic image and improving a real-time recall rate. Besides, an observation situation of the target object may be known in time according to the corresponding target endoscopic image frame outputted by the medical device.

The endoscopic image processing method provided in this application is described below by using an example in which a polyp (a foreign body) in a colon image is determined by using an endoscopic video stream. Various medical images are generated by an endoscopic device, for example, images are generated continuously as an endoscope continuously performs photographing in digestive tract, and the images further become a large amount of data, so that it is urgently required to implement large-scale classification and identification with the aid of execution of classification prediction.

In view of this, the artificial intelligence (AI) technology provides a properly-trained auxiliary analytical information forming network to support the foregoing applied solution. AI involves a theory, a method, a technology, and an application system that use a digital computer or a machine controlled by the digital computer to simulate, extend, and expand human intelligence, perceive an environment, obtain knowledge, and use knowledge to obtain an optimal result. AI is to study design principles and implementation methods of various intelligent machines, to enable the machines to have functions of perception, reasoning, and decision-making. In the AI medical field, identification of low-latency videos and messages is implemented by using a digital computer or a machine controlled by the digital computer, to obtain auxiliary analytical information conveniently according to a pathological analysis result.

However, in the related art, a target detection model using various types of target detection algorithms such as Retina Net, FasterRCNN, and YOLO with relatively high accuracy is generally integrated in a solution to implementing target detection on an endoscopic video stream (such as a colon endoscopic video stream), and image frames in the video stream are sequentially inputted into the model for target detection. However, a processing speed of the model is limited, and the processing speed of the model cannot match a speed of a real-time video stream (most detection models cannot keep pace with a frame rate of a real-time video), thereby impairing an output of the model.

In the related art, a process of processing an original endoscopic image carried in the endoscopic video stream by using a neural network model to determine the polyp (the foreign body) includes:

1) Directly processing image frames in a real-time video stream by using the neural network model. However, a frame rate of the real-time video stream is generally not less than 25 fps and a frame interval is less than 40 ms, and the model processing speed cannot match the speed of the real-time video stream.
2) Only extracting a part of frames from the video stream for detection (for example, extraction is performed at intervals of N frames), and skipping processing video frames that are not processed in time (frame-skipping processing).
3) Adding a tracking algorithm (for example, various types of target tracking algorithms such as KCF, CSRDCF, SiamFC, or SiamRPN) based on conventional detection. For example, a segment processing method is used, where an initial frame is found by the detection model, and target positioning is performed by placing detection with tracking in subsequent stages. Although this solution can ensure the real-time capability to some extent, the accuracy of polyp detection may be reduced. Alternatively, a model integration method is used, where the tracking algorithm is regarded as another detection model, and the detection model and tracking algorithm are performed on all frames. Although this solution can ensure the accuracy of polyp detection, however, the real-time capability is reduced, which does not support continuous use by a doctor.

With reference to summary of the related art, in the conventional process of processing a colon endoscopic video stream by using a neural network model, defects mainly include:

1) The detection model processing consumes long time and cannot keep pace with a video frame rate, the detection is stopped, and an effect is distorted.

When the speed of the detection model cannot keep pace with the frame rate of the real-time video stream, a common phenomenon is that: a picture detection box is stopped, the detection box stayed at an original place, but a target in the video is no longer at the original place. Under a specific evaluation value indicator, this phenomenon may cause a serious decrease in real-time image accuracy, a real-time recall rate, and a real-time F value. From the perspective of user's visual experience, this phenomenon may cause a decrease in user experience, and for a doctor, not only diagnosis experience is seriously affected, but also the chance of missed detection may be increased.

2) The detection model has low stability and poor robustness.

In a changeable and unpredictable scene of a video stream, performance of the detection model jitters easily and is not stable. Such trigger scenes include: a lens is blur, a lens changes rapidly, a target deforms, a target is partially blocked, and a target comes in and goes out at a visual field boundary.

3) Lack of ID identification of the same target.

The detection model does not include an ID identification function of the same target. In a target detection use scenario, it is desirable to trigger a warning or prompt when finding a new target, but the robustness of the detection model is relatively low and the model lacks of an ID identification function of the same target, so that repeated warnings/prompts are often triggered, which may easily generate unnecessary disturbance to a user.

Figure 5:
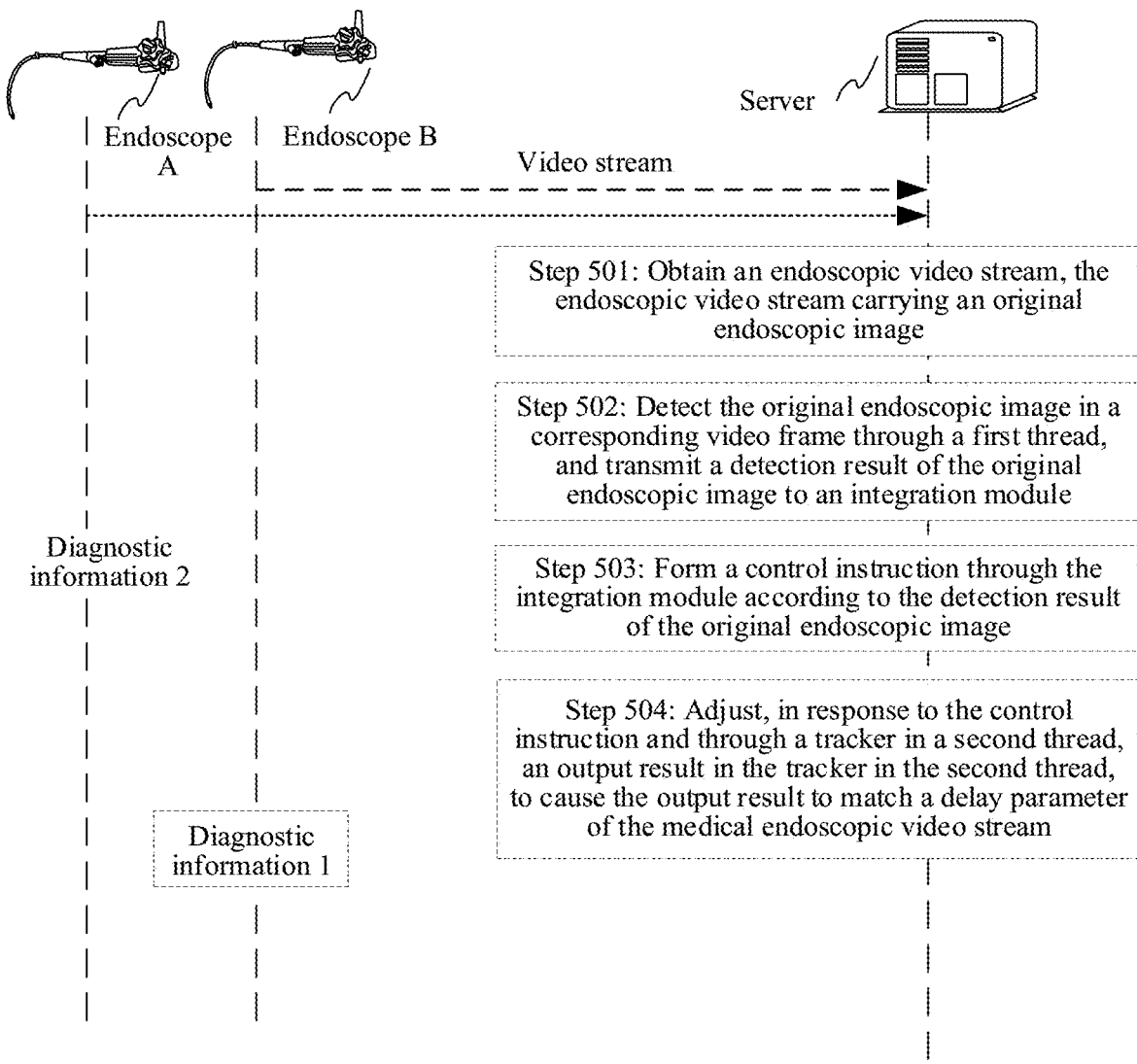
FIG. 5 is a schematic flowchart of an endoscopic image processing method according to an embodiment consistent with this disclosure.

FIG. 5 is a schematic flowchart of an endoscopic image processing method according to an embodiment consistent with this disclosure, where the user may be a user operating a colon endoscope, and the method specifically includes the following steps:

Step 501: Obtain an endoscopic video stream, the endoscopic video stream carrying an original endoscopic image.

Step 502: Detect the original endoscopic image in a corresponding video frame through a first thread, and transmit a detection result of the original endoscopic image to an integration module.

Step 503: Form a control instruction through the integration module according to the detection result of the original endoscopic image.

Step 504: Adjust, in response to the control instruction and through a tracker in a second thread, an output result in the tracker in the second thread, to cause the output result to match a delay parameter of the endoscopic video stream, the first thread and the second thread being parallel threads.

Figure 6:
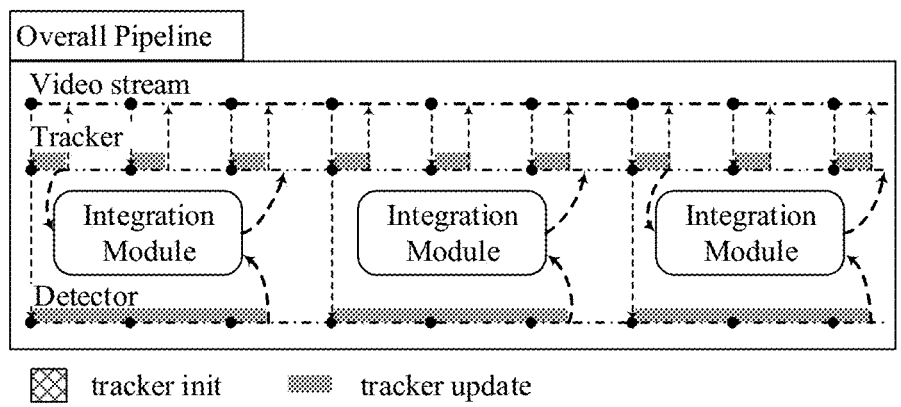
FIG. 6 is a schematic diagram of different threads in an endoscopic image processing method according to an embodiment consistent with this disclosure.

FIG. 6 is a schematic diagram of different threads in an endoscopic image processing method according to an embodiment consistent with this disclosure. In the figure:

1) In a timeline of an endoscopic video stream, each point represents one frame, if an input frame rate of a real-time video is 25 fps, a point/frame interval represents 40 ms, and the rest may be deduced by analogy.

2) Tracker: all outputted detection boxes are provided by the tracker in real time, and the tracker directly controls video outputs.

3) Detector: the detector maintains and instructs a next action of the tracker by using an integration module, and indirectly controls video outputs.

4) Intersected dotted line: represents information transmission between components, start time points and end time points of information transmission may be noted.

The tracker is responsible for ensuring the real-time capability and improving the robustness; and the tracker may receive a control instruction of the integration module, to directly return a detection box to the video stream in real time. Further, the tracker used in the second thread needs to meet a low-latency requirement, so that any low-latency real-time tracker such as CSR-DCF or SiamRPN based on manual features may be used to implement direct information exchange with the video stream.

The detector is responsible for ensuring the accuracy. Specifically, the detector may transmit a corresponding control instruction by using the integration module, to implement initialization, continuous working, re-initiation, and stop of the tracker.

The detector does not need to meet a real-time requirement, and if a previous frame is not completed, detection of the frame is given up. Any detector algorithm such as YOLOv3, RetinaNet, or FasterRCNN may be used, and the detector does not directly perform information exchange with the video stream.

The integration module is responsible for collecting information of two parallel lines, and the detector and the integration module are jointly adjusted.

Referring to FIG. 7 to FIG. 10, in a working process of the tracker in the second thread, states of the tracker include: a wait state; an initiation state; a continuation state; a re-initiation state; and a stop state.

The wait state indicates that the detector does not find any target, and the tracker is in a wait state.

Figure 7:
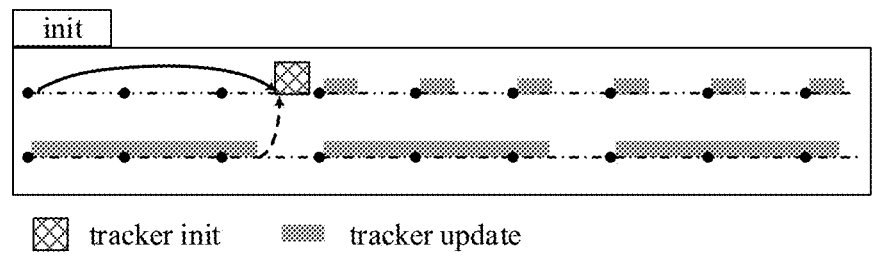
FIG. 7 is a schematic diagram of an initiation state in an endoscopic image processing method according to an embodiment consistent with this disclosure.

FIG. 7 is a schematic diagram of an initiation state in an endoscopic image processing method according to an embodiment consistent with this disclosure. The initiation state indicates that the detector finds a first frame target and a bbox bounding-box regression parameter thereof, and the tracker is activated and initialized by using the box regression parameter.

Figure 8:
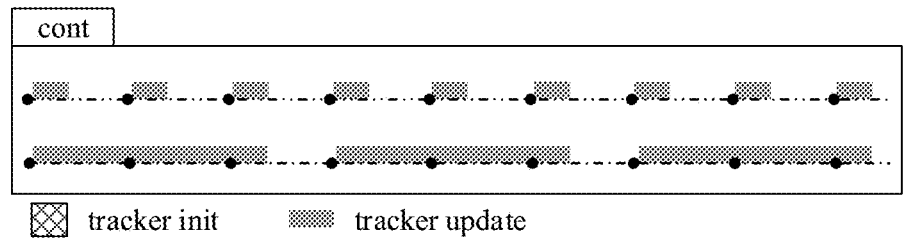
FIG. 8 is a schematic diagram of a continuation state in an endoscopic image processing method according to an embodiment consistent with this disclosure.

FIG. 8 is a schematic diagram of a continuation state in an endoscopic image processing method according to an embodiment consistent with this disclosure. The continuation state indicates that in a tracking process, if a box provided by the tracker highly overlaps with an instruction box provided by the detector (IoU≥µ), it indicates that the target is still well tracked by the tracker (the target does not depart), so that the tracker keeps tracking the target.

Figure 9:
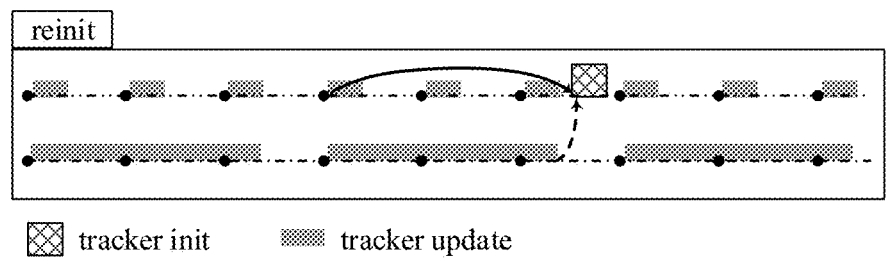
FIG. 9 is a schematic diagram of a re-initiation state in an endoscopic image processing method according to an embodiment consistent with this disclosure.

FIG. 9 is a schematic diagram of a re-initiation state in an endoscopic image processing method according to an embodiment consistent with this disclosure. The re-initiation state indicates that in a tracking process, if an degree of overlap between a box provided by the tracker and an instruction box provided by the detector is low (IoU≤μ), where μ may be dynamically adjusted according to the use environment of the endoscopic video stream, it indicates that the tracker loses the target or tracking of the target is not accurate, so that bbox of the detector is used to reactivate and initialize the tracker.

Figure 10:
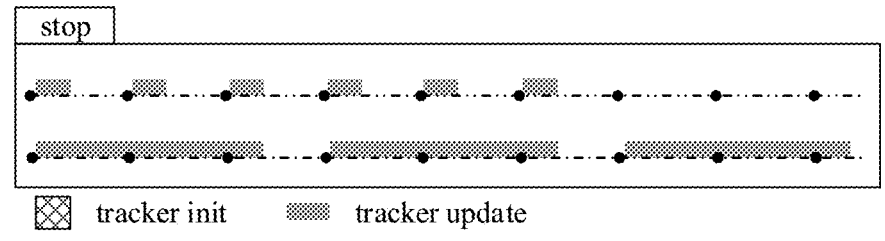
FIG. 10 is a schematic diagram of a re-initiation state in an endoscopic image processing method according to an embodiment consistent with this disclosure.

FIG. 10 is a schematic diagram of a re-initiation state in an endoscopic image processing method according to an embodiment consistent with this disclosure. The stop state indicates that in a tracking process, if the detector does not find an effective target in N consecutive frames, it indicates that the target may be not in a visual field already, so that the tracker is stopped.

Figure 11:
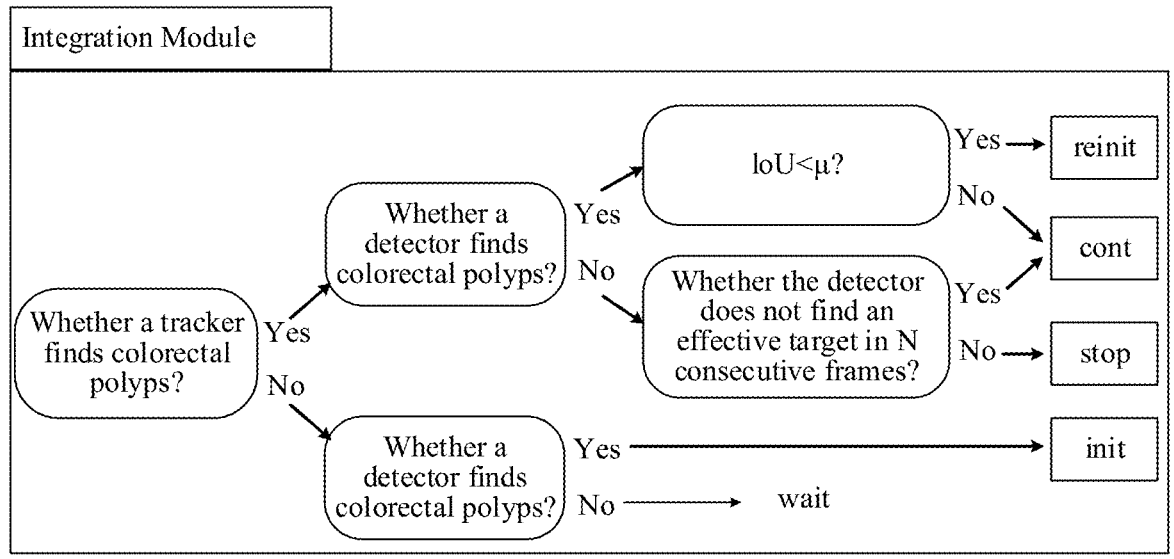
FIG. 11 is a schematic diagram of a determination process on the same target in an endoscopic image processing method according to an embodiment consistent with this disclosure.

FIG. 11 is a schematic diagram of a determination process on the same target in an endoscopic image processing method according to an embodiment consistent with this disclosure, where the endoscopic image processing method provided in this application is used to perform detection on an endoscopic video stream of a patient.

1) appearance of a new target: a target in an initiation state is regarded as a new target that is found for the first time, and a new ID is allocated to the target; and
2) maintenance of an old target: targets in an initiation state, a continuation state, and a re-initiation state are regarded as the same target, and an ID during initialization is allocated to the target. According to the foregoing identification strategies, warnings and prompts of a repeated target may be reduced, thereby reducing unnecessary disturbance to the user.

In a process of determining a polyp in a colon image by using the endoscopic image processing method (an asynchronous in parallel detection and tracking (AIPDT) solution) provided in this application, the performance of the endoscopic image processing method may be monitored.

Video evaluation of the endoscopic video stream needs to consider a video frame rate. Often, a real-time frame rate is 25 fps, namely, each frame is 40 ms, and if a time consumed by the model exceeds 40 ms, a result of a previous frame is directly used as a current result (represented as a stopped picture output). Based on the priori evaluation, indicators shown in table 1 are calculated:

TABLE 1

| Indicator dimension | Indicator description |
| --- | --- |
| Speed (indicator) | One indicator: an average latency of a single frame, unit: ms (If the frame rate of the video stream is 25 fps, a real-time standard is reached when the latency is less than 40 ms) |
| Accuracy (indicator) | Four indicators: real-time accuracy, real-time recall rate, real-time F1 value, and real-time F2 value, unit: percentage |

When the detection algorithm uses YOLOv3, and the tracking algorithm uses CSR-DCF,
(1) For improvement of the speed indicator, refer to table 2,

TABLE 2

| Indicator | Average latency of a single frame |
| --- | --- |
| Conventional solution (Detector solution) | 84.7 ms |
| AIPDT solution | 24.4 ms |

If the detector uses RetinaNet or a more complex network, the latency of the detector solution generally falls within 100 ms to 200 ms.

(2) For improvement of the real-time accuracy, refer to table 3,

TABLE 3

| Indicator | Real-time accuracy | Real-time recall rate | Real-time F1 | Real-time F2 |
| --- | --- | --- | --- | --- |
| Conventional solution (Detector solution) | 92.48 | 85.13 | 88.65 | 86.51 |
| AIPDT solution | 96.23 | 90.19 | 93.11 | 91.33 |

Figure 12:
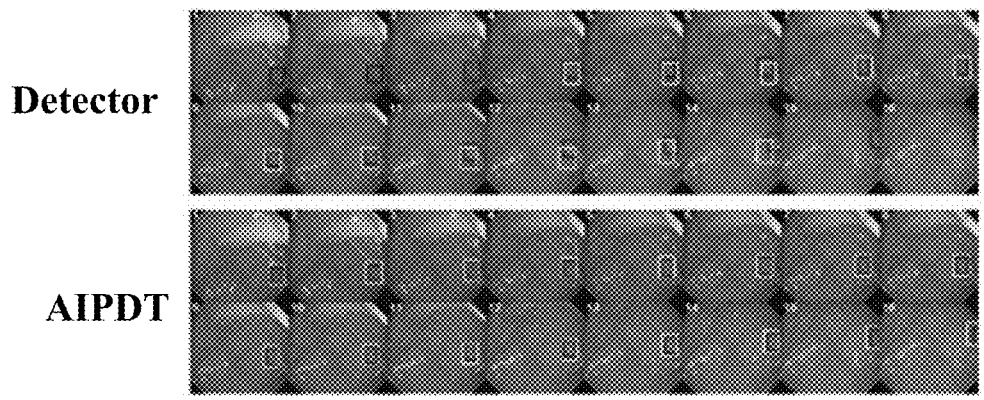
FIG. 12 is a schematic diagram of a display of an endoscopic image processing method according to an embodiment consistent with this disclosure.

FIG. 12 is a schematic diagram of a display of an endoscopic image processing method according to an embodiment consistent with this disclosure. Due to high latency in the conventional technology (the Detector solution), tracking boxes corresponding to the tracker cannot match foreign body boxes corresponding to the detector, many tracking boxes continue to use a result of a previous frame, leading to a decrease in the accuracy and the recall rate, and a serious decrease in a visual effect of the endoscopic image. According to the endoscopic image processing method (AIPDT) provided in the embodiments consistent with this disclosure, positions of the tracking boxes are more accurate and match with the foreign body boxes, and the robustness is better, which facilitates continuous working of the endoscope.

The term module, and other similar terms such as subunit, unit, submodule, etc., in this disclosure may refer to a software unit, a hardware unit, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each unit can be part of an overall module that includes the functionalities of the module.

In some embodiments, the computer-readable storage medium may include: a read-only memory (ROM), a random access memory (RAM), a solid state drive (SSD), an optical disc, or the like. The RAM may include a resistance random access memory (ReRAM) and a dynamic random access memory (DRAM). The sequence numbers of the foregoing embodiments consistent with this disclosure are merely for description purpose but do not imply the preference among the embodiments.

Beneficial Technical Effects

An endoscopic video stream is obtained, where the endoscopic video stream carries an original endoscopic image; the original endoscopic image in a corresponding video frame is detected through a first thread, and a detection result of the original endoscopic image is transmitted to an integration module; a control instruction is formed through the integration module according to the detection result of the original endoscopic image; and in response to the control instruction and through a second thread, an output result in the second thread is adjusted. The first thread and the second thread are parallel threads, so that the output result may match a use environment of the endoscopic video stream, thereby improving real-time accuracy of processing on the endoscopic image and improving a real-time recall rate.

The foregoing descriptions are merely embodiments consistent with this disclosure, but are not intended to limit the protection scope of this application. Any modification, equivalent replacement and improvement made within the spirit and principle of this application shall fall within the protection scope of this application.

INDUSTRIAL APPLICATIONS

In embodiments consistent with this disclosure, an endoscopic video stream is obtained, the endoscopic video stream carrying an original endoscopic image; the original endoscopic image in a corresponding video frame is detected through a first thread, and a detection result of the original endoscopic image is transmitted to an integration module; a control instruction is formed through the integration module according to the detection result of the original endoscopic image; and in response to the control instruction and through a second thread, an output result in the second thread is adjusted, to make the output result to match a use environment of the endoscopic video stream. The first thread and the second thread are parallel threads, so that the output result may be controlled to match the use environment of the endoscopic video stream by using the first thread and the second thread that are parallel, thereby improving real-time accuracy of processing on the endoscopic image and improving a real-time recall rate.

What is claimed is:

1. An endoscopic image processing method, performed by an electronic device, the endoscopic image processing method comprising:
   obtaining an endoscopic video stream, the endoscopic video stream including an original endoscopic image;
   detecting the original endoscopic image in a corresponding video frame through a first thread, and transmitting a detection result of the original endoscopic image to an integration module, comprising:
      detecting a foreign body through a detector in the first thread to obtain a foreign body box distributed in a target endoscopic image frame, the target endoscopic image frame being obtained based on the original endoscopic image, and the foreign body box indicating a region where the foreign body exists in the target endoscopic image frame;
      filtering the target endoscopic image frame based on the foreign body box, to position a lesion region in the target endoscopic image frame and determine a lesion category; and
      transmitting the lesion region in the target endoscopic image frame to the integration module;
   forming a control instruction through the integration module according to the detection result; and
   adjusting, in response to the control instruction and through a second thread, an output result in the second thread, the output result corresponding to a use environment of the endoscopic video stream, the first thread and the second thread being parallel threads.

2. The method according to claim 1, wherein the obtaining an endoscopic video stream comprises:
   extracting an endoscopic video frame in pathological information of a target object;
   improving resolution of the endoscopic video frame;
   converting a format of the endoscopic video frame from a current encoding format to a grayscale value encoding format, to obtain a plurality of endoscopic video frames; and
   performing encoding compression on the endoscopic video frame to form an endoscopic video stream.

3. The method according to claim 2, wherein the converting a format of the endoscopic video frame from a current encoding format to a grayscale value encoding format comprises:
   performing encoding compression on the endoscopic video frame using an encoding method corresponding to a target format;
   writing a serial number corresponding to the video frame and generating a timestamp corresponding to an image packet, to generate a packet corresponding to the format of the endoscopic video frame; and
   splicing the image packet to form a plurality of endoscopic video frames.

4. The method according to claim 1, wherein the method further comprises:
   adjusting the original endoscopic image to a target size to generate standard endoscopic image frames; and
   filtering the standard endoscopic image frames and deleting a standard endoscopic image frame having interference, to form the target endoscopic image frame comprising different target endoscopic image frames.

5. The method according to claim 1, wherein the method further comprises:
   when a detection time of the detector in the first thread exceeds a detection time threshold, stopping detecting a current target endoscopic image frame, and obtaining a subsequent target endoscopic image frame for detection.

6. The method according to claim 1, wherein the adjusting, in response to the control instruction and through a second thread, an output result in the second thread comprises:
   when a tracker in the second thread is in a continuation state and a tracking box corresponding to the tracker matches a foreign body box corresponding to a detector, outputting, by the tracker in the second thread, a current target endoscopic image frame; or
   when a tracker in the second thread is in a re-initiation state and a tracking box corresponding to the tracker does not match a foreign body box corresponding to a detector, outputting, by the tracker in the second thread, a new target endoscopic image frame.

7. The method according to claim 6, wherein the method further comprises:
   determining a corresponding box regression parameter when a foreign body box exists in the target endoscopic image frame; and
   activating the tracker in the second thread by using the box regression parameter.

8. The method according to claim 7, wherein the method further comprises:
   when the tracker in the second thread is activated, distributing a target identifier to a foreign body in the current target endoscopic image frame; and
   when foreign bodies in target endoscopic image frames when the tracker in the second thread is in an activated state, a continuation state, and a re-initiation state are consistent, initializing the target identifier to implement continuous tracking on the foreign body in the current target endoscopic image frame.

9. The method according to claim 1, wherein the method further comprises:
   transmitting an adjustment instruction in response to the output result in the second thread, the adjustment instruction adjusting a detection state of a medical device in contact with a target object, to obtain new pathological information.

10. An electronic device, comprising:
a memory, configured to store executable instructions; and
a processor, configured to, when executing the executable instructions stored in the memory, perform:
obtaining an endoscopic video stream, the endoscopic video stream including an original endoscopic image;
detecting the original endoscopic image in a corresponding video frame through a first thread, and transmitting a detection result of the original endoscopic image to an integration module comprising:
detecting a foreign body through a detector in the first thread to obtain a foreign body box distributed in a target endoscopic image frame, the target endoscopic image frame being obtained based on the original endoscopic image, and the foreign body box indicating a region where the foreign body exists in the target endoscopic image frame;
filtering the target endoscopic image frame based on the foreign body box, to position a lesion region in the target endoscopic image frame and determine a lesion category; and
transmitting the lesion region in the target endoscopic image frame to the integration module;
forming a control instruction through the integration module according to the detection result; and
adjusting, in response to the control instruction and through a second thread, an output result in the second thread, the output result corresponding to a use environment of the endoscopic video stream, the first thread and the second thread being parallel threads.

11. A non-transitory computer-readable storage medium, storing executable instructions, the executable instructions, when executed by a processor, implementing:
obtaining an endoscopic video stream, the endoscopic video stream including an original endoscopic image;
detecting the original endoscopic image in a corresponding video frame through a first thread, and transmitting a detection result of the original endoscopic image to an integration module comprising:
detecting a foreign body through a detector in the first thread to obtain a foreign body box distributed in a target endoscopic image frame, the target endoscopic image frame being obtained based on the original endoscopic image, and the foreign body box indicating a region where the foreign body exists in the target endoscopic image frame;
filtering the target endoscopic image frame based on the foreign body box, to position a lesion region in the target endoscopic image frame and determine a lesion category; and
transmitting the lesion region in the target endoscopic image frame to the integration module;
forming a control instruction through the integration module according to the detection result; and
adjusting, in response to the control instruction and through a second thread, an output result in the second thread, the output result corresponding to a use environment of the endoscopic video stream, the first thread and the second thread being parallel threads.

12. The computer-readable storage medium according to claim 11, wherein the obtaining an endoscopic video stream comprises:
extracting an endoscopic video frame in pathological information of a target object;
improving resolution of the endoscopic video frame;
converting a format of the endoscopic video frame from a current encoding format to a grayscale value encoding format, to obtain a plurality of endoscopic video frames; and
performing encoding compression on the endoscopic video frame to form an endoscopic video stream.

13. The computer-readable storage medium according to claim 12, wherein the converting a format of the endoscopic video frame from a current encoding format to a grayscale value encoding format comprises:
performing encoding compression on the endoscopic video frame using an encoding method corresponding to a target format;
writing a serial number corresponding to the video frame and generating a timestamp corresponding to an image packet, to generate a packet corresponding to the format of the endoscopic video frame; and
splicing the image packet to form a plurality of endoscopic video frames.

14. The computer-readable storage medium according to claim 11, wherein the executable instructions further causes the processor to implement:
adjusting the original endoscopic image to a target size to generate standard endoscopic image frames; and
filtering the standard endoscopic image frames and deleting a standard endoscopic image frame having interference, to form the target endoscopic image frame comprising different target endoscopic image frames.

15. The computer-readable storage medium according to claim 11, wherein the executable instructions further causes the processor to implement:
when a detection time of the detector in the first thread exceeds a detection time threshold, stopping detecting a current target endoscopic image frame, and obtaining a subsequent target endoscopic image frame for detection.

16. The computer-readable storage medium according to claim 11, wherein the adjusting, in response to the control instruction and through a second thread, an output result in the second thread comprises:
when a tracker in the second thread is in a continuation state and a tracking box corresponding to the tracker matches a foreign body box corresponding to a detector, outputting, by the tracker in the second thread, a current target endoscopic image frame; or
when a tracker in the second thread is in a re-initiation state and a tracking box corresponding to the tracker does not match a foreign body box corresponding to a detector, outputting, by the tracker in the second thread, a new target endoscopic image frame.

17. The computer-readable storage medium according to claim 16, wherein the executable instructions further causes the processor to implement:
determining a corresponding box regression parameter when a foreign body box exists in the target endoscopic image frame; and
activating the tracker in the second thread by using the box regression parameter.

18. The computer-readable storage medium according to claim 17, wherein the executable instructions further causes the processor to implement:
when the tracker in the second thread is activated, distributing a target identifier to a foreign body in the current target endoscopic image frame; and
when foreign bodies in target endoscopic image frames when the tracker in the second thread is in an activated state, a continuation state, and a re-initiation state are consistent, initializing the target identifier to implement continuous tracking on the foreign body in the current target endoscopic image frame.

* * * * *